United States Patent
Rautenberg-Groth et al.

(10) Patent No.: US 10,925,369 B2
(45) Date of Patent: Feb. 23, 2021

(54) PERMANENT WAVING METHOD WITH IMPROVED NOURISHING AND WAVE EFFECT

(71) Applicant: Henkel AG & Co. KGaA, Duesseldorf (DE)

(72) Inventors: Birgit Rautenberg-Groth, Ellerau (DE); Matthias Schweinsberg, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 550 days.

(21) Appl. No.: 15/335,544

(22) Filed: Oct. 27, 2016

(65) Prior Publication Data

US 2017/0119122 A1  May 4, 2017

(30) Foreign Application Priority Data

Nov. 3, 2015  (DE) .......................... 10 2015 221 460

(51) Int. Cl.
| | | |
|---|---|---|
| *A61Q 5/04* | (2006.01) | |
| *A45D 7/04* | (2006.01) | |
| *A45D 40/24* | (2006.01) | |
| *A61K 8/19* | (2006.01) | |
| *A61K 8/22* | (2006.01) | |
| *A61K 8/24* | (2006.01) | |
| *A61K 8/362* | (2006.01) | |
| *A61K 8/37* | (2006.01) | |
| *A61K 8/41* | (2006.01) | |
| *A61K 8/44* | (2006.01) | |
| *A61K 8/46* | (2006.01) | |
| *A61K 8/55* | (2006.01) | |
| *A61K 8/73* | (2006.01) | |
| *A61K 8/84* | (2006.01) | |
| *B65D 85/00* | (2006.01) | |

(52) U.S. Cl.
CPC .............. *A45D 7/04* (2013.01); *A45D 40/24* (2013.01); *A61K 8/19* (2013.01); *A61K 8/22* (2013.01); *A61K 8/24* (2013.01); *A61K 8/362* (2013.01); *A61K 8/37* (2013.01); *A61K 8/41* (2013.01); *A61K 8/416* (2013.01); *A61K 8/44* (2013.01); *A61K 8/46* (2013.01); *A61K 8/55* (2013.01); *A61K 8/73* (2013.01); *A61K 8/84* (2013.01); *A61Q 5/04* (2013.01); *B65D 85/70* (2013.01); *A61K 2800/87* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,858,337 | A | * | 1/1999 | Watatani .................. A61K 8/19 132/210 |
| 2008/0025937 | A1 | * | 1/2008 | Cassier .................. A61K 8/416 424/70.2 |
| 2008/0025939 | A1 | * | 1/2008 | Cassier .................. A61K 8/447 424/70.5 |

FOREIGN PATENT DOCUMENTS

| | | |
|---|---|---|
| DE | 69209725 T2 | 10/1996 |
| DE | 19710154 A1 | 9/1998 |
| DE | 10120306 A1 | 10/2002 |
| DE | 102004050561 A1 | 4/2006 |
| EP | 1812117 A1 | 8/2007 |
| EP | 0689827 A1 | 1/2019 |
| GB | 773559 A | 4/1957 |
| WO | 2007096045 A1 | 8/2007 |

\* cited by examiner

*Primary Examiner* — Jyothsna A Venkat
(74) *Attorney, Agent, or Firm* — P. Scott Smith

(57) ABSTRACT

A method for permanently changing the shape of keratinic fibres and a kit-of-parts comprising the agents (a), (b) and (c) packaged separately. The method comprises applying a permanent waving agent (a) to the keratinic fibres, leaving agent (a) to take effect for a period of from 2-60 minutes, rinsing out the agent (a) from the keratinic fibres, applying agent (b) to the keratinic fibres, leaving agent (b) to take effect for a period of from 2-60 minutes, rinsing out agent (b) from the keratinic fibres, applying agent (c) to the keratinic fibres, leaving agent (c) to take effect for a period of from 2-60 minutes, and rinsing out agent (c) from the keratinic fibres. The permanent waving agent (a) includes one or more keratin-reducing compounds, the cosmetic agent (b) includes one or more aliphatic $C_2$-$C_8$ dicarboxylic acids and/or physiologically acceptable salts thereof, and the fixing agent (c) includes hydrogen peroxide.

8 Claims, No Drawings

PERMANENT WAVING METHOD WITH IMPROVED NOURISHING AND WAVE EFFECT

FIELD OF THE INVENTION

The present invention generally relates to cosmetics, and more particularly relates to methods for permanently changing the shape of keratinic fibres, in particular human hair, which methods are characterised by the successive use of a first permanent waving agent, a second intermediate treatment agent, and a third fixing agent. Here, each of these three agents is applied to the keratinic fibres, left to take effect, and rinsed out again, before the next agent is applied to the keratin fibres. A further subject of the present invention is a multi-component packaging unit (kit-of-parts) for permanently changing the shape of the keratinic fibres, which unit comprises the three agents in separately packaged containers.

BACKGROUND OF THE INVENTION

A permanent change to the shape of keratinic fibres is usually carried out such that the fibres are mechanically deformed and the deformation is fixed by suitable aids (for example curlers, rollers). Before and/or after this deformation, the fibres are treated with the aqueous preparation of a keratin-reducing substance and are rinsed with water or an aqueous solution following an exposure time. In a second step, the fibres are then treated with the aqueous preparation of an oxidising agent. Following an exposure time, this is also rinsed out, and the fibres are freed from the mechanical deformation aids.

A change of shape to the keratin fibres which is permanent and stable with respect to the influence of water can be achieved only as a result of chemical interventions in the hair which aim to cleave the cystine disulphide bonds found in hair keratin. This cleaving is usually performed under the influence of keratin-reducing substances. These are reducing agents which cleave some of the disulphide bonds of the keratin to form —SH— groups, thus resulting in a relaxation of the peptide cross-linking. Due to the stress of the keratin fibres wound onto a roller, the keratin structure is re-oriented. Under the influence of the oxidising agent, disulphide bonds are linked again, and the keratin structure is in this way re-fixed in the predefined deformation. A known method of this type is the permanent waving treatment of human hair. This can be used both to produce curls and waves in straight hair and to straighten curly hair.

The permanent waving treatment results in curled hair which is internally stressed, includes new (reductively or oxidatively modified) amino acids, and is incompletely cross-linked. This can lead to a gradual, slow relaxation of the deformation, i.e. the curls drop out. A further negative side-effect of permanently waved hair is often damage to the hair structure, since both the hair interior and the surface of the hair become more hydrophilic due to the combination of reduction and oxidation step. For this reason, high humidity, frequent hair washing, and also combing and brushing can lead to a reduction of the wave effect on the damaged hair. New agents and permanent waving methods are still sought, with which all of these known disadvantages can be avoided.

The object was therefore to find new methods and agents for the permanent deformation of keratinic fibres, which methods and agents have an intensified, long-lasting wave effect and at the same time nourish the hair to the greatest extent possible.

Surprisingly, it has now been found that this object can be achieved optimally when the keratin fibres are permanently waved or permanently deformed in a method in which three special agents are used in succession.

Furthermore, other desirable features and characteristics of the present invention will become apparent from the subsequent detailed description of the invention and the appended claims, taken in conjunction with this background of the invention.

BRIEF SUMMARY OF THE INVENTION

A method for permanently changing the shape of keratinic fibres, in particular human hair, comprising the following steps in the specified order: A1) applying a permanent waving agent (a) to the keratinic fibres; A2) leaving the permanent waving agent (a) to take effect for a period of from 2 to 60 minutes; A3) rinsing out the permanent waving agent (a) from the keratinic fibres; B1) applying a cosmetic agent (b) to the keratinic fibres; B2) leaving the cosmetic agent (b) to take effect for a period of from 2 to 60 minutes; B3) rinsing out the cosmetic agent (b) from the keratinic fibres; C1) applying a fixing agent (c) to the keratinic fibres; C2) leaving the fixing agent (c) to take effect for a period of from 2 to 60 minutes; C3) rinsing out the fixing agent (c) from the keratinic fibres, wherein the permanent waving agent (a) (a1) includes one or more keratin-reducing compounds, and the cosmetic agent (b) (b1) includes one or more aliphatic $C_2$-$C_8$ dicarboxylic acids and/or physiologically acceptable salts thereof, and the fixing agent (c) (c1) includes hydrogen peroxide.

A multi-component packaging unit (kit-of-parts) for permanently changing the shape of keratinic fibres, in particular human hair, which comprises, packaged separately from one another, a container (A) containing a permanent waving agent (a); and a container (B) containing a cosmetic agent (b); and a container (C) containing a fixing agent (c), wherein the permanent waving agent (a) in container (A) (a1) includes one or more keratin-reducing compounds, and the cosmetic agent (b) in container (B) (b1) includes one or more aliphatic $C_2$-$C_8$ dicarboxylic acids and/or physiologically acceptable salts thereof, and (b2) one or more alkalising agents, and the fixing agent (c) in container (C) (c1) includes hydrogen peroxide.

Use of aliphatic $C_2$-$C_8$ dicarboxylic acids and/or the physiologically acceptable salts hereof to intensify the effect of permanent shape-changing agents on human hair.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present invention is a method for permanently changing the shape of keratinic fibres, in particular human hair, comprising the following steps in the specified order A1) applying a permanent waving agent (a) to the keratinic fibres, A2) leaving the permanent waving agent (a) to take effect for a period of from 2 to 60 minutes, A3) rinsing out the permanent waving agent (a) from the keratinic fibres, B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide.

Keratinic fibres, keratin-containing fibres or keratin fibres are understood to be furs, wool, feathers and in particular human hair. Although the agents according to the invention are primarily suitable for permanently changing the shape of keratin fibres, there is in principle nothing standing in the way of use in other fields as well.

Permanently changing the shape of keratinic fibres is understood to mean a change in shape with which a reducing agent is first applied to the keratin fibres, followed by an oxidising agent. Due to the influence of the reducing agent, the reductive cleaving of the cystine disulphide bonds found in the hair occurs first. During the deformation process, the hair is brought into its new shape with the aid of mechanical deformation aids (for example curlers, rollers, etc.). The mechanical deformation of the hair can take place here before, during, or after the application of the reducing agent. By applying the oxidising agent, new disulphide bonds are formed in the deformed keratin fibres, and the keratin fibres are fixed in this way. As a general rule, the permanent change in shape withstands multiple hair washes.

The following steps A), B), and C) are characterising and essential for the method according to the invention:
A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) optionally rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres.

A permanent waving agent (a) is firstly applied to the keratinic fibres (step A1)), is left there to take effect for a period of from 2 to 60 minutes (step A2)), and is then rinsed off again (step A3)). The agent (a) can be rinsed off here either only using mains water, or with the aid of a shampoo or conditioner, for example.

The permanent waving agent (a) includes at least one keratin-reducing compound and can also contain mixtures of a plurality of keratin-reducing compounds.

A feature of the method according to the invention that is essential to the invention is the fact that the reducing agent-containing permanent waving agent (a) is rinsed off from the keratin fibres before the cosmetic agent (b) is applied to the keratin fibres.

Here, it is indeed possible, but not necessary, for the keratinic fibres to be dried following the rinsing off of the agent (a) (i.e. after step A3)). The agent (b) is preferably applied to keratin fibres that are still slightly damp or to towel-died keratin fibres.

The cosmetic agent (b) is an intermediate treatment agent, i.e. the agent (b) is applied to the keratinic fibres once the permanent waving agent (a) has been rinsed off (step B1)), is left to take effect on the keratinic fibres (step B2)), and is then rinsed off again (step B3)).

The intermediate treatment agent (b) includes at least one aliphatic $C_2$-$C_8$ dicarboxylic acid.

The agent (b) can be rinsed off for example either only using mains water or with the aid of a shampoo or conditioner. Here, it is indeed possible, but not necessary for the keratinic fibres to be dried following the rinsing off of the agent (b) (i.e. after step B3)). The agent (c) is preferably applied to keratin fibres that are still slightly damp or to towel-died keratin fibres.

Once the intermediate treatment agent (b) has been rinsed off, the oxidizing agent-containing fixing agent (c) is then applied to the keratin fibres (step C1)). The fixing agent is also left to take effect on the keratin fibres (step C2)) and is then rinsed off again (step C3)). The agent (c) can also be rinsed off for example either using only mains water or with the aid of a shampoo or conditioner.

The fixing agent (c) includes hydrogen peroxide as oxidising agent.

The three agents (a), (b) and (c) are each left to take effect for a period of from 2 to 60 minutes in steps A2, B2), and C2) respectively. The exposure time for the agent (a) is preferably 5 to 15 min, more preferably 10 to 45 min, and particularly preferably 15 to 40 min. The exposure time for the agent (b) is preferably 5 to 50 min, more preferably 7 to 35 min, and particularly preferably 10 to 25 min. The exposure time for the agent (c) is preferably 5 to 50 min, more preferably 10 to 45 min, and particularly preferably 15 to 40 min.

A preferred embodiment is therefore a method for permanently changing the shape of keratinic fibres, in particular human hair, comprising the following steps in the specified order
A1) applying a permanent waving agent (a) to the keratinic fibres,
A2) leaving the permanent waving agent (a) to take effect for a period of from 10 to 45 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 7 to 35 minutes,
B3) rinsing out the cosmetic agent (b) from the keratinic fibres,
C1) applying a fixing agent (c) to the keratinic fibres,
C2) leaving the fixing agent (c) to take effect for a period of from 10 to 45 minutes,
C3) rinsing out the fixing agent (c) from the keratinic fibres, wherein
the permanent waving agent (a)
(a1) includes one or more keratin-reducing compounds and the cosmetic agent (b)
(b1) includes one or more aliphatic $C_2$-$C_8$ dicarboxylic acids and/or physiologically acceptable salts thereof, and the fixing agent (c)
(c1) includes hydrogen peroxide.

A further particularly preferred embodiment is a method for permanently changing the shape of keratinic fibres, in particular human hair, comprising the following steps in the specified order A1) applying a permanent waving agent (a) to the keratinic fibres,
A2) leaving the permanent waving agent (a) to take effect for a period of from 15 to 40 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 10 to 25 minutes,
B3) rinsing out the cosmetic agent (b) from the keratinic fibres,
C1) applying a fixing agent (c) to the keratinic fibres,
C2) leaving the fixing agent (c) to take effect for a period of from 15 to 40 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide.

In a process for permanently changing shape, the change in shape to the keratin fibres or hair is implemented by using a mechanical deformation aid. By way of example, the strands of hair can thus firstly be wound individually onto curlers and then treated with the agents (a), (b) and (c). However, it is also possible to first treat the hair with the reducing agent (a), rinse this off, then wind their hair onto the curlers and then apply agents (b) and (c).

A preferred embodiment is therefore a method for permanently changing the shape of keratinic fibres, in particular human hair, comprising the following steps in the specified order A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide, and
the keratinic fibres are deformed with the aid of deformation aids before, after, or during step A1), A2), A3), B1), B2), B3), C1), C2) and/or C3).

A deformation which is performed after, before, or during step A1) to C3) is understood to mean a deformation which is performed chronologically directly before, during, or after one of steps A1) to C3), i.e. the time distance between applying the curler and the application of the particular agent is a few minutes or most one hour or a few hours.

Deformation aids in the sense of the method according to the invention can be, for example, curlers, rollers, or clips in the case of permanent waving, or aids the mechanical straightening, such as a comb or a brush or a straightening board in the case of hair straightening.

A particularly preferred embodiment is a method for permanently changing the shape of keratinic fibres, in particular human hair, comprising the following steps in the specified order deforming the keratin fibres with the aid of deformation aids,
A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide.

A further particularly preferred embodiment is also a method of permanently changing the shape of keratinic fibres, in particular human hair, comprising the following steps in the specified order A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
deforming the keratin fibres with the aid of deformation aids,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres, C1) applying a fixing agent (c) to the keratinic fibres,
C2) leaving the fixing agent (c) to take effect for a period of from 2 to 60 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide.

A particularly preferred embodiment is also a method for permanently changing the shape of keratinic fibres, in particular human hair, comprising the following steps in the specified order
A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
deforming the keratin fibres with the aid of deformation aids,
C1) applying a fixing agent (c) to the keratinic fibres,
C2) leaving the fixing agent (c) to take effect for a period of from 2 to 60 minutes,
C3) rinsing out the fixing agent (c) from the keratinic fibres, wherein
the permanent waving agent (a)
(a1) includes one or more keratin-reducing compounds and
the cosmetic agent (b)
(b1) includes one or more aliphatic $C_2$-$C_8$ dicarboxylic acids and/or physiologically acceptable salts thereof, and
the fixing agent (c)
(c1) includes hydrogen peroxide.

In the previously described method according to the invention, the three agents (a), (b) and (c) are used in succession. These three agents for carrying out the method are advantageously made available to the user in the form of a multi-component packaging unit, i.e. a kit-of-parts.

A second subject of the present invention is a multi-component packaging unit (kit-of-parts) for permanently changing the shape of keratinic fibres, in particular human hair, which comprises, packaged separately from one another,
a container (A) containing a permanent waving agent (a), and
a container (B) containing a cosmetic agent (b), and
a container (C) containing a fixing agent (c),
wherein
the permanent waving agent (a) in container (A)
(a1) includes one or more keratin-reducing compounds, and the cosmetic agent (b) in container (B)
(b1) includes one or more aliphatic $C_2$-$C_8$ dicarboxylic acids and/or physiologically acceptable salts thereof, and
(b2) one or more alkalising agents, and
the fixing agent (c) in container (C)
(c1) includes hydrogen peroxide.

The kit-of-parts according to the invention comprises at least three separately packaged containers (A), (B) and (C), which contain the three agents (a), (b) and (c). The permanent waving agent (a) is disposed in the container (A) and includes at least one keratin-reducing compound. The intermediate treatment agent (b) is disposed in the container (B) and includes at least one aliphatic $C_2$-$C_8$ dicarboxylic acid (b1) and at least one alkalising agent (b2). Lastly, the fixing agent (c) is disposed in the container (C) and includes hydrogen peroxide.

A characterising feature, essential to the invention, of the permanent waving agent (a) is it content of at least one reducing agent able to reductively cleave the disulphide bonds present in the hair keratin and convert these into thiol groups —SH. Reducing agents of this type are referred to within the scope of this invention as keratin-reducing compounds.

Suitable reducing agents are thioglycolic acid, thiolactic acid, thiomalic acid, cysteine, cysteamine, cysteine, 2-mercaptoethanesulfonic acid and/or also the physiologically acceptable salts of these acids. A physiologically acceptable salt is understood to mean a salt of the aforementioned compounds, which have been converted into their ionic form and which has a physiologically acceptable counter ion. A physiologically acceptable salt can be applied to the hair and to the skin without any toxicological disadvantages, i.e. a physiologically acceptable salt of an aforementioned reducing agent is not poisonous and is not more sensitising than a reducing agent itself. Physiologically acceptable salts are, for example, the alkali metals results, the alkaline earth metals salts, or the ammonium salts of the aforementioned acids.

A particularly suitable method according to the invention and a particularly suitable kit-of-parts are characterised in that the permanent waving agent (a) includes
(a1) one or more keratin-reducing compounds from the group of thioglycolic acid, thiolactic acid, thiomalic acid, cysteine, cysteamine, cysteine, 2-mercaptoethanesulfonic acid and/or the physiologically acceptable salts thereof.

Thiolactic acid is understood to mean D-thiolactic acid, L-thiolactic acid and/or a mixture thereof. Thiolactic acid is alternatively also referred to as 2-mercaptopropionic acid and has the CAS number 79-42-5. Suitable physiologically acceptable salts are, for example, the sodium salt, the potassium salt, or the ammonium salt of thiolactic acid.

Ammonium thioglycolate is the ammonium salt of thioglycolic acid (i.e. the ammonium salt of 2-sulfanylacetic acid) (formula I)

(formula I)

Thiolactic acid is understood to mean D-thiolactic acid, L-thiolactic acid and/or a mixture thereof. Thiolactic acid is alternatively also referred to as 2-mercaptopropionic acid and has the CAS number 79-42-5. Suitable physiologically acceptable salts are, for example, the sodium salt, the potassium salt, or the ammonium salt of thiolactic acid.

Ammonium thiolactate is the ammonium salt of thiolactic acid (i.e. the ammonium salt of 2-sulfanylpropionic acid) (formula II).

Thiomalic acid is a compound of formula (III). Thiomalic acid is understood to mean D-thiomalic acid, L-thiomalic acid and/or a mixture thereof. Suitable physiologically acceptable salts are the sodium salt, the potassium salt, or the ammonium salt of thiomalic acid.

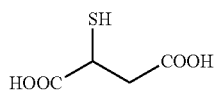

Cysteine is understood to mean D-cysteine, L-cysteine and/or a mixture thereof. Cysteine is alternatively also referred to as 2-amino-3-mercaptopropanoic acid or 2-amino-3-sulfanylpropanoic acid. Suitable physiologically acceptable salts are the sodium salt, the potassium salt, or the ammonium salt of cysteine.

Cysteamine is alternatively also referred to as 2-aminoethanol and has the formula HS—CH$_2$—CH$_2$—NH$_2$. Suitable physiologically acceptable salts of cysteamine are, for example, the hydrochloride, the hydrobromide, the sulphate, or the hemisulfate.

Cystine is a disulphide produced by oxidation of two molecules of the amino acid cysteine. Cystine has the CAS number 56-89-3. The definition of cystine also includes the (D,D), (D,L), (L,D) and (L,L) isomers. Suitable physiologically acceptable salts are the sodium salt, the potassium salt, or the ammonium salt of cystine.

2-mercaptoethanesulfonic acid is a compound of formula (IV). Suitable physiologically acceptable salts are, for example, the sodium salt, the potassium salt, or the ammonium salt of 2-mercaptoethanesulfonic acid.

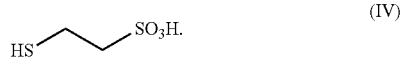

The aforementioned reducing agents are commercially obtainable from various providers (Sigma Aldrich, Merck, Fluka or Alfa Aesar etc.).

It has been found that certain reducing agents are particularly well suited for use in the method and kit-of-parts according to the invention. Thioglycolic acid, ammonium thioglycolate, thiolactic acid and/or ammonium thiolactate are very particularly preferred, since a particularly good improvement of the wave force is observed with use of these reducing agents with subsequent application of the intermediate treatment agent (b).

A particularly suitable method according to the invention and a particularly suitable kit-of-parts are characterised in that the permanent waving agent (a) includes
(a1) one or more keratin-reducing compounds from the group of thioglycolic acid, ammonium thioglycolate, thiolactic acid and/or ammonium thiolactate.

The permanent waving agent (a) includes the keratin-reducing compound(s) preferably in certain quantity ranges which ensure a satisfactory deformation, without damaging the keratin fibres too heavily. The permanent waving agent (a) particularly preferably includes one or more keratin-reducing compounds in a total quantity of from 1.5 to 20.0% by weight, preferably 3.0 to 15.0% by weight, more preferably from 4.0 to 12.0% by weight, and particularly preferably from 4.5 to 12.5% by weight. Here, all specified quantities are based on the total weight of the keratin-reducing compounds, in relation to the total weight of the agent (a).

A particularly suitable method according to the invention and a particularly suitable kit-of-parts are characterised in that the permanent waving agent (a)—in relation to the total weight of the permanent waving agent (a)—includes
(a1) one or more keratin-reducing compounds in a total quantity of from 1.5 to 20.0% by weight, preferably 3.0 to 15.0% by weight, more preferably from 4.0 to 12.0% by weight, and particularly preferably from 4.5 to 12.5% by weight.

A characterising feature essential to the invention of the agent (b) is its content of one or more aliphatic $C_2$-$C_8$ dicarboxylic acids.

Aliphatic $C_2$-$C_8$ dicarboxylic acids in the sense of the present invention can be saturated or unsaturated. When the dicarboxylic acids are unsaturated, they can comprise one or more double bonds, which can be present in each case in cis or trans configurations. The $C_2$-$C_8$ dicarboxylic acids according to the invention are aliphatic, i.e. they comprise no aromatic grouping. Furthermore, the $C_2$-$C_8$ dicarboxylic acids according to the invention can also do carry further substituents, such as one or more oxo groups, or hydroxyl groups. The acids are characterised by the presence of two acid groups (i.e. two carboxyl groups). Tricarboxylic acids (such as citric acid) therefore are not dicarboxylic acids in the sense of the present invention.

The aliphatic $C_2$-$C_8$ dicarboxylic acids can also be used in the form of their physiologically acceptable salts. Examples of physiologically acceptable salts are the sodium salts, the potassium salts, or the ammonium salts of $C_2$-$C_8$ dicarboxylic acids.

During the course of the work carried out for this invention, it was found that a particularly good wave results could be attained on keratin vipers that had been treated by means of the method according to the invention when the intermediate treatment agent (b) contained one or more acids from the group of maleic acid, succinic acid, fumaric acid, oxalic acid, malonic acid, tartaric acid, malic acid, 2-oxo-succinic acid, 2-hydroxymalonic acid and/or the physiologically acceptable salts of these compounds.

A particularly suitable method according to the invention and a particularly suitable kit-of-parts are characterised in that the agent (b) includes
(b1) one or more aliphatic $C_2$-$C_8$ dicarboxylic acids from the group of maleic acid, succinic acid, fumaric acid, oxalic acid, malonic acid, tartaric acid, malic acid, 2-oxo-succinic acid, 2-hydroxymalonic acid and/or the physiologically acceptable salts of these compounds.

Maleic acid is alternatively also referred to as cis-butenedioic acid and has the CAS number 110-16-7. Suitable physiologically acceptable salts of maleic acid are the sodium salt, the potassium salt or the ammonium salt.

Succinic acid, also referred to as succinyl acid or 1,4-butanedioic acid, is a colourless, crystalline, aliphatic dicarboxylic acid. The crystals are easily soluble in boiling water. Succinic acid has the CAS number 110-15-6. Suitable physiologically acceptable salts of succinic acid are the sodium salt, the potassium salt or the ammonium salt.

Fumaric acid is the trivial name of trans-butenedioic acid. Fumaric acid has the CAS number 110-17-8. Suitable physiologically acceptable salts of fumaric acid are the sodium salt, the potassium salt or the ammonium salt.

Oxalic acid is alternatively referred to as 1,2-ethanedioic acid. The anhydrous compound has the CAS number 144-62-7. The dehydrate of oxalic acid can also be used and has the CAS number 6153-56-6. Suitable physiologically acceptable salts of oxalic acid are the sodium salt, the potassium salt or the ammonium salt.

The alternative name for malonic acid is 1,3-propanedioic acid. Malonic acid has the CAS number 141-82-2. Suitable physiologically acceptable salts of malonic acid are the sodium salt, the potassium salt or the ammonium salt.

Tartaric acid, also referred to as 2,3-dihydroxysuccinic acid or 2,3-dihydroxybutanedioic acid or L-tartaric acid, has the CAS numbers 87-69-4 [L-(+) form], 147-71-7 [D-(−) form], 147-73-9 [meso form], 133-37-9 [DL-(±) form]. All stereoisomers of tartaric acid and mixtures thereof correspond to the invention. The salts of tartaric acid are also referred to as tartrates. Suitable physiologically acceptable salts of tartaric acid are the sodium salt, the potassium salt or the ammonium salt.

Malic acid is alternatively also referred to as 2-hydroxysuccinic acid, 2-hydroxybutanedioic acid, or 2-hydroxybutane-1,4-dioic acid. Malic acid has the CAS numbers 97-67-6 [L-(−) malic acid], 636-61-3 [D-(+) malic acid] and 6915-15-7 [DL-(±) malic acid]. All stereoisomers of malic acid and mixtures thereof correspond to the invention. Suitable physiologically acceptable salts of malic acid are the sodium salt, the potassium salt or the ammonium salt.

2-oxo-succinic acid is also referred to as oxaloacetic acid or 2-oxo-1,4-butanedioic acid and has the CAS number 328-42-7. The salts of 2-oxo-succinic acid are referred to as oxaloacetates. Suitable physiologically acceptable salts of 2-oxo-succinic acid are the sodium salt, the potassium salt or the ammonium salt.

The trivial name of 2-hydroxymalonic acid with the CAS number 80-69-3 is tartronic acid. Suitable physiologically acceptable salts of 2-hydroxymalonic acid are the sodium salt, the potassium salt or the ammonium salt.

The best results with regard to wave intensity and nourishing effect were obtained when the acids maleic acid, succinic acid, fumaric acid, mixtures of these acids and/or the physiologically acceptable salts of these acids were used in the cosmetic agent (b).

An explicitly very particularly suitable method according to the invention and a particularly suitable kit-of-parts are characterised in that the agent (b) includes
(b1) one or more aliphatic $C_2$-$C_8$ dicarboxylic acids from the group of maleic acid, succinic acid, fumaric acid and/or the physiologically acceptable salts thereof.

An explicitly very particularly suitable method according to the invention and a particularly suitable kit-of-parts are, in other words, characterised in that the agent (b) includes
(b1) one or more aliphatic $C_2$-$C_8$ dicarboxylic acids from the group of maleic acid, the sodium salt of maleic acid, the potassium salt of maleic acid, the ammonium salt of maleic acid, succinic acid, the sodium salt of succinic acid, the potassium salt of succinic acid, the ammonium salt of succinic acid, fumaric acid, the sodium salt of fumaric acid, the potassium salt of fumaric acid and/or the ammonium salt of fumaric acid.

The intermediate treatment agent (b) preferably includes the aliphatic $C_2$-$C_8$ dicarboxylic acids according to the invention in certain quantity ranges. A visible intensification of the wave effect is attained even with use of just small acid quantities. However, it is particularly advantageous when the intermediate treatment agent (b) according to the invention includes one or more aliphatic $C_2$-$C_8$ dicarboxylic acids in a total quantity of from 0.1 to 25.0% by weight, preferably from 2.5 to 20.0% by weight, more preferably from 6.5 to 18.0% by weight, and particularly preferably from 9.5 to 17.5% by weight. Here, all specified quantities are based on the total weight of all aliphatic $C_2$-$C_8$ dicarboxylic acids contained in the agent (b), in relation to the total weight of the agent (b). In particular, a used quantity from 9.5 to 17.5% by weight makes it possible to attain an excellent deformation result with simultaneous reduction of the exposure time.

An explicitly very particularly suitable method according to the invention and a particularly suitable kit-of-parts are characterised in that the agent (b)—based on the total weight of the agent (b)—includes
(b1) one or more aliphatic $C_2$-$C_8$ dicarboxylic acids and/or the physiologically acceptable salts hereof in a total quantity of from 0.1 to 25.0% by weight, preferably from 2.5 to 20.0% by weight, more preferably from 6.5 to 18.0% by weight, and particularly preferably from 9.5 to 17.5% by weight.

Besides the aliphatic $C_2$-$C_8$ dicarboxylic acids (b1), the intermediate treatment agent (b) very particularly preferably additionally includes one or more alkalising agents (b2). Without being limited to a theory, the alkalising agents appear to convert the $C_2$-$C_8$ dicarboxylic acids according to the invention into their salts, which, possibly via the formation of salt bridges, are responsible for the increase in wave intensity. It has thus been found that the strength and durability of the permanent deformation can be optimised further still with use of the combination of $C_2$-$C_8$ dicarboxylic acid (b1) and alkalising agent (b2).

By way of example, basic amino acids such as arginine, lysine, ornithine and/or histidine can be used in the intermediate treatment agent (b).

An explicitly very particularly suitable method according to the invention and a particularly suitable kit-of-parts are characterised in that the agent (b) includes
(b2) one or more alkalising agents from the group composed of arginine, lysine, ornithine and/or histidine.

Further suitable alkalising agents are inorganic alkalising agents from the group composed of sodium hydroxide, potassium hydroxide, sodium carbonate, sodium hydrogen carbonate, potassium carbonate, potassium hydrogen carbonate and/or ammonium carbonate.

A particularly suitable method according to the invention and a particularly suitable kit-of-parts are characterised in that the agent (b) includes
(b2) one or more alkalising agents from the group composed of sodium hydroxide, potassium hydroxide, sodium carbonate, sodium hydrogen carbonate, potassium carbonate, potassium hydrogen carbonate and/or ammonium carbonate.

Lastly, alkalising agents from the group composed of ammonia and alkanolamines have proven to be very particularly suitable for use in the agent (b).

A particularly suitable method according to the invention and a particularly suitable kit-of-parts are characterised in that the agent (b) includes
(b2) one or more alkalising agents from the group composed of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol and/or 2-amino-2-methylpropan-1,3-diol.

The agent (b) can also contain a number of alkalising agents. It is furthermore explicitly very particularly preferred when the agent (b) includes (b2') one or more alkalising agents from the group composed or arginine, lysine, ornithine and/or histidine, and additionally (b2") one or more alkalising agents from the group composed of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol and/or 2-amino-2-methylpropan-1,3-diol.

It has been found that the method and kit-of-parts according to the invention achieve the object particularly effectively when the pH value of agent (b) lies in the range of from 4.5 to 12.0, preferably from 5.5 to 11.0, more preferably from 7.5 to 11.0, and very particularly preferably from 9.0 to 10.5. In this case, the agent (b) has an aqueous or water-containing cosmetic carrier.

The pH values of the present invention were measured using a glass electrode of the N 61 type from Schlott at a temperature of 22° C.

A particularly suitable method according to the invention and a particularly suitable kit-of-parts are characterised in that the agent (b) is aqueous or includes water and has a pH value of from 4.5 to 12.0, preferably from 5.5 to 11.0, more preferably from 7.5 to 11.0, and very particularly preferred from 9.0 to 10.5.

A particularly strong wave effect having particularly good durability was attained when the cosmetic intermediate treatment agent (b) contained one of the following combinations of aliphatic C2-C8 diacids (b1) and alkalising agent (b2). For this reason, the three embodiments described hereinafter are explicitly most preferred.

An explicitly very particularly suitable method according to the invention and a particularly suitable kit-of-parts are characterised in that the agent (b)—based on the total weight of the agent (b)—includes
 (b1) 7.5 to 17.5% by weight maleic acid and/or succinic acid and
 (b2) 5.0 to 15.0% by weight 2-aminoethan-1-ol*monoethanolamine) and
 (b3) water.

An explicitly very particularly suitable method according to the invention and a particularly suitable kit-of-parts are characterised in that the agent (b)—based on the total weight of the agent (b)—includes
 (b1) 7.5 to 17.5% by weight maleic acid and/or succinic acid and
 (b2) 1.0 to 10.0% by weight arginine and/or histidine, and
 (b3) water.

An explicitly very particularly suitable method according to the invention and a particularly suitable kit-of-parts are characterised in that the agent (b)—based on the total weight of the agent (b)—includes
 (b1) 7.5 to 17.5% by weight maleic acid and/or succinic acid and
 (b2) 2.0 to 10.0% by weight potassium hydroxide and/or sodium hydroxide, and
 (b3) water.

A further preferred method according to the invention and a particularly suitable kit-of-parts are lastly also characterised in that the ratio by weight of all aliphatic $C_2$-$C_8$ dicarboxylic acids (b1) contained in the agent (b) to all alkalising agents (b2) contained in the agent (b), i.e. the ration by weight of (b1)/(b2), lies at a value of from 1.0 to 5.0, preferably from 1.2 to 3.8, more preferably from 1.3 to 2.5, and very particularly preferably from 1.4 to 2.2.

Example: 100 g of an intermediate treatment agent (b) according to the invention contain
15.0% by weight maleic acid (b1)
10.0% by weight ethanolamine (b2)
0.3% by weight arginine (b2)
The ratio by weight of (b1)/(b2) is (15.0/[10.0+0.3])=1.46

Following the application, exposure and rinse-off of the agent (b), the fixing agent (c) is then applied in the method according to the invention. The fixing agent (c) can preferably be applied to damp or towel-dried hair. The fixing agent (c) includes hydrogen peroxide (c1) as oxidising agent. The disulphide bonds in the deformed keratin are re-linked by the oxidising agent, and the deformed strands are fixed in their new shape in this way.

The fixing agent (c) includes hydrogen peroxide in a cosmetic carrier. In a preferred embodiment hydrogen peroxide itself is used as aqueous solution in the fixing agent (c). The concentration of a hydrogen peroxide solution is determined here on the one hand by the legal stipulations and on the other hand by the desired effect; 1.5 to 12% by weight solutions in water are preferably used. Fixing agents (c) that are preferred in accordance with the invention are characterised in that they contain 1.0 to 15.0% by weight, preferably 2.0 to 12.0% by weight, more preferably 3.0 to 9.0% by weight, and very particularly preferably 3.5 to 7.5% by weight of hydrogen peroxide, in each case based on the total weight of the fixing agent (c).

In a further preferred embodiment a method and kit-of-parts according to the invention are therefore characterised in that the fixing agent (c)—based on the total weight of the agent (c)—includes
 (c1) 1.0 to 15.0% by weight, preferably 2.0 to 12.0% by weight, more preferably 3.0 to 9.0% by weight, and very particularly preferably 3.5 to 7.5% by weight of hydrogen peroxide.

The agents (a), (b) and (c) contain all previously mentioned essential ingredients usually in a cosmetic carrier. The cosmetic carrier can be a suitable aqueous, alcoholic, or aqueous-alcoholic carrier. By way of example, the agents (a), (b) and (c) can each be applied to the keratinic fibres in the form of a cream, an emulsion, a gel, or also in the form of a surfactant-containing foaming solution, such as a shampoo, a foam aerosol, a foam formulation, or in the form of another preparation suitable for application to the hair.

The agents (a), (b) and (c) according to the invention can additionally contain further wave force-intensifying components, such as heterocyclic compounds, such as imidazole, pyrrolidine, piperidine, dioxolane, dioxane, morpholine and piperazine and derivatives of these compounds, such as the $C_{1-4}$ alkyl derivatives, $C_{1-4}$ hydroxyalkyl derivatives, and $C_{1-4}$ aminoalkyl derivatives. Preferred substituents which can be positioned both at carbon atoms and at nitrogen atoms of the heterocyclic ring systems are methyl, ethyl, β-hydroxyethyl and β-aminoethyl groups. Derivatives of heterocyclic compounds that are preferred in accordance with the invention are, for example, 1-methylimidazole, 2-methylimidazole, 4(5)-methylimidazole, 1,2-dimethylimidazole, 2-ethylimidazole, 2-isopropylimidazole, N-methylpyrrolidone, 1-methylpiperidine, 4-methylpiperidine, 2-ethylpiperidine, 4-methylmorpholine, 4-(2-hydroxyethyl)morpholine, 1-ethylpiperazine, 1-(2-hydroxyethyl)piperazine, 1-(2-aminoethyl)piperazine. Imidazole derivatives also preferred in accordance with the invention are biotin, hydantoin and benzimidazole. Imidazole is very particularly preferred.

Amino acids (in the agents (a) and/or (c)) such as, in particular, arginine, citrulline, histidine, ornithine and lysine. The amino acids can be used both as free amino acid and as salts, such as hydrochlorides. Furthermore, oligopeptides from an average of 2-3 amino acids which have a high proportion (>50%, in particular >70%) of the specified amino acids have also proven to be usable in accordance with the invention. Arginine and salts thereof and arginine-rich oligopeptides are particularly preferred in accordance with the invention.

Diols, such as 2-ethyl-1,3-hexanediol, 1,3-butanediol, 1,4-butanediol, 1,2-propanediol, 1,3-propanediol, neopentyl glycol and ethylene glycol. 1,3-diols, in particular 2-ethyl-1,3-hexanediol and 1,3-butanediol, have proven to be particularly well suited.

The agents (a), (b) and (c) according to the invention can additionally contain at least one oil component. Oil components that are suitable in accordance with the invention are, in principle, all oils and lipid substances and mixtures thereof with solid paraffins and waxes. Oil components of which the solubility in water at 20° C. is less than 1% by weight, in particular less than 0.1% by weight, are preferred. The melt requirement of the individual oil or fat components lies preferably below approximately 40° C. Oil components which are liquid at room temperature, i.e. below 25° C., can be particularly preferred in accordance with the invention. With use of a number of oil and fat components and optionally solid paraffins and waxes, however, it is generally also sufficient when the mixture of the oil and fat components and optionally paraffins and waxes meets these conditions.

A preferred group of oil components is constituted by vegetable oils. Examples of such oils are apricot kernel oil, avocado oil, sunflower oil, olive oil, soybean oil, rapeseed oil, almond oil, jojoba oil, orange oil, wheat germ oil, peach kernel oil and the liquid components of coconut oil. Other triglyceride oils are also suitable, however, such as the liquid components of beef tallow and synthetic triglyceride oils.

A further particularly preferred group of oil components that can be used in accordance with the invention is constituted by liquid paraffin oils and synthetic hydrocarbons and also di-n-alkylethers having a total of between 12 and 36 C atoms, in particular 12 to 24 C atoms, such as di-n-octylethers, di-n-decylethers, di-n-nonylethers, di-n-undecylethers, di-n-dodecylethers, n-hexyl-n-octylethers, n-octyl-n-decylethers, n-decyl-n-undecylethers, n-undecyl-n-dodecylethers and n-hexyl-n-undecylethers and di-tert-butylethers, di-iso-pentylethers, di-3-ethyldecylethers, tert.-butyl-n-octylethers, iso-pentyl-n-octylethers and 2-methyl-pentyl-n-octylethers. The compounds 1,3-di-(2-ethylhexyl)-cyclohexane (Cetiol® S) and di-n-octylether (Cetiol® OE), which are obtainable as commercial products, can be preferred.

Oil components that can be used in accordance with the invention are also fatty acid and fatty alcohol esters. The monoesters of fatty acids with alcohols having 2 to 24 C atoms are preferred. This substance group is constituted by the products of esterification of fatty acids having 8 to 24 C atoms, such as caproic acid, caprylic acid, 2-ethylhexanoic acid, capric acid, lauric acid, isotridecanoic acid, myristic acid, palmitic add, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, which occur for example in the event of the pressure-splitting of natural fats and oils, in the event of reduction of aldehydes from Roelens oxosynthesis, or the dimerisation of unsaturated fatty acids, with alcohols such as isopropyl alcohol, glycerol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachyl alcohol, gadoleyl alcohol, behenyl alcohol, erucyl alcohol and brassidyl alcohol and technical mixtures thereof, which occur for example in the event of high-pressure hydrogenation of technical-grade methyl esters based on fats and oils or aldehydes from Roelens oxosynthesis, and also as monomer fraction in the event of the dimerisation of unsaturated fatty alcohols. Isopropyl myristate, isononanoic acid C16-C18 alkyl ester (Cetiol® SN), stearic acid 2-ethylhexyl ester (Cetiol® 868), cetyl oleate, glycerol tricaprylate, coconut fatty alcohol caprinate/caprylate and n-butyl stearate are particularly preferred in accordance with the invention.

Dicarboxylic acid esters such as di-n-butyl adipate, di-(2-ethylhexyl) adipate, di-(2-ethylhexyl) succinate and di-isotridecyl acelaat, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, and neopentyl glycol dicaprylate are also oil components that can be used in accordance with the invention, as well as complex esters such as diacetyl glycerol monostearate.

Oil components that can be used with preference in accordance with the invention are, lastly, also silicone oils, in particular dialkyl and alkylaryl siloxanes, such as dimethyl polysiloxane and methylphenyl polysiloxane and alkoxylated and quaternised analogues thereof and cyclic siloxanes. Examples of such silicones are the products marketed by Dow Corning under the names of DC 190, DC 200 and DC 1401 and the commercial products DC 344 and DC 345 of Dow Corning, Q2-7224 (manufacturer: Dow Corning; a stabilised trimethyl silyl amodimethicone), Dow Corning® 929 emulsion (containing a hydroxyl amino-modified silicone which is also known as Amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80). Silicone oils having a kinematic viscosity up to 50,000 cSt measured at 25° C. can be preferred in the context of the invention. Silicone oils having kinematic viscosities up to 10,000 cSt measured at 25° C. are very particularly preferred. The viscosities are determined here by the ball drop method in accordance with the "British Standard 188" method. Comparable values are obtained using manufacturer's test procedures similar to the "British Standard 188" method, for example the "CTM 0577" test procedure of the Dow Corning Corporation.

In a particular embodiment, cyclic siloxanes are used in particular as oil components, such as the products Dow Corning® 344, Dow Corning® 345, Dow Corning® 244, Dow Corning® 245 or Dow Corning® 246 having kinematic viscosities of up to 10,000 cSt determined at 25° C. in accordance with the manufacturer's instructions.

Oil components that can be used in accordance with the invention are lastly also dialkyl carbonates, as described in detail in DE OS19710154, to which reference is made expressly. Dioctyl carbonates, in particular the di-2-ethylhexyl carbonate, are preferred oil components within the scope of the present invention.

The agents according to the invention can also contain alcohols which can be mixed with water only to a limited extent.

The expression "can be mixed with water only to a limited extent" is understood to mean alcohols which are soluble in water at 20° C. to an extent of no more than 10% by weight, based on the water mass.

In many cases, triols and in particular diols have proven to be particularly suitable in accordance with the invention. Alcohols having 4 to 20, in particular 4 to 10 carbon atoms can be used in accordance with the invention. The alcohols used in accordance with the invention can be saturated or unsaturated and linear, branched or cyclic. By way of example, butanol-1, cyclohexanol, pentanol-1, decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, caprin alcohol, linoleyl alcohol, linolenyl alcohol and behenyl alcohol, and the guerbet alcohols thereof can be used in the context of the invention, wherein this list is intended to be exemplary and non-limiting. The fatty alcohols, however, preferably originate from natural fatty acids, wherein recovery from the esters of fatty acids by reduction can usually be assumed. Fatty alcohol cuts which are produced by reduction of naturally occurring triglycerides, such as beef tallow, palm oil, peanut oil, rapeseed oil, cottonseed oil, soybean oil, sunflower oil and linseed oil, or fatty acid esters formed from the transesterification products thereof with corresponding alcohols and which therefore represent a mixture of different fatty alcohols can also be used in accordance with the invention.

2-ethylhexanediol-1,3, butanol-1, cyclohexanol, pentanol-1 and 1,2-butanedio are preferred as alcohols in accordance with the invention. 2-ethylhexanediol-1,3, but also butanol-1 and cyclohexanol are particularly preferred.

In a further embodiment emulsifiers can be used in the agents according to the invention. Emulsifiers cause the formation of water-stable or oil-stable adsorption layers at the phase interface, which layers protect the dispersed droplets against coalescence and thus stabilise the emulsion. Emulsifiers are therefore constructed from a hydrophobic and a hydrophilic molecule part, similarly to surfactants. Hydrophilic emulsifiers preferably form O/W emulsions and hydrophobic emulsifiers preferably form W/O emulsions. An emulsion is to be understood to mean a droplet-like distribution (dispersion) of one liquid in another liquid with expenditure of energy to create stabilising phase boundaries by means of surfactants. The selection of these emulsifying surfactants or emulsifiers is focused here on the substances to be dispersed and the particular outer phase and the fineness of the emulsion. More detailed definitions and properties of emulsifiers can be found in "H.-D. Dörfler, Grenzflächen- and Kolloidchemie, VCH Verlagsgesellschaft mbH. Weinheim, 1994" (Interface and Colloid Chemistry, VCH publishing group mbH). Emulsifiers that can be used in accordance with the invention are, for example, Addition products of from 4 to 100 mol ethylene oxide and/or 0 to 5 mol propylene oxide with linear fatty alcohols having 8 to 22 C atoms, with fatty acids having 12 to 22 C atoms, and with alkyl phenols having 8 to 15 C atoms in the alkyl group, $C_{12}$-$C_{22}$ fatty acid mono esters or diesters of addition products of from 1 to 30 mol ethylene oxide with polyols having 3 to 6 carbon atoms, in particular with glycerol, Ethylene oxide and polyglycerol addition products with methyl glucoside fatty acid esters, fatty acid alkanolamides and fatty acid glucamides, $C_8$-$C_{22}$ alkyl mono glycosides and alkyl oligo glycosides and ethoxylated analogues thereof, wherein oligomerisation degrees of from 1.1 to 5, in particular 1.2 to 2.0, and glucose are preferred as sugar components, Mixtures of alkyl (oligo) glucosides and fatty alcohols, for example the commercially obtainable product Montanov®68, Addition products of from 5 to 60 mol ethylene oxide with castor oil and hardened castor oil, Partial esters of polyols having 3-6 carbon atoms with saturated fatty acids having 8 to 22 C atoms, Sterols. Sterols are understood to be a group of steroids which carry a hydroxyl group at C atom 3 of the steroid skeleton and which are isolated both from animal tissue (zoosterols) and from vegetable fats (phytosterols). Examples of zoosterols are cholesterol and lanosterol. Examples of suitable phytosterols are ergosterol, stigmasterol and sitosterol. Sterols are also isolated from fungi and yeasts, i.e. what are known as mycosterols.

Phospholipids. These are understood to be, in particular, the glucose phospholipids, which for example are obtained as lecithins or phosphatidylcholines from, for example, egg yolk or plant seeds (for example soybeans).

Fatty acid esters of sugars and sugar alcohols, such as sorbitol.

Polyglycerols and polyglycerol derivatives, such as polyglycerol poly-12-hydroxystearate (commercial product Dehymuls® PGPH), Linear and branched fatty acids having 8 to 30 C atoms, and Na, K, Ca, Mg and Zn salts thereof.

The agents according to the invention contain the emulsifiers preferably in quantities of from 0.1 to 25% by weight, in particular 0.1 to 3% by weight, based on the particular total composition.

The agents according to the invention can preferably contain at least one non-ionogenic emulsifier having an HLB value of from 8 to 18, in accordance with the definitions detailed in Römpp-Lexikon Chemie (Römpp's Chemistry Lexicon) (Hrg. J. Falbe, M. Regitz), 10$^{th}$ edition, Georg Thieme publishers Stuttgart, N.Y., (1997), page 1764. Non-ionogenic emulsifiers having an HLB value of 10-15 can be particularly preferred in accordance with the invention.

The agent according to the invention is present in the form of a water-containing agent. A water-containing agent in the sense of the invention includes at least 40% by weight water based on the weight of the total agent. The eater-containing agent according to the invention can be present in various forms, for example as a lotion, oil-in-water emulsion, or water-in-oil emulsion.

The teaching according to the invention, however, also includes embodiments of the agent according to the invention in which a multi-phase agent is present which can be produced from two or more separately packaged starting preparations only immediately before application. This embodiment can be preferred in the case of incompatible constituents. It has surprisingly been found that wave agents formulated in this way provide a significantly increased wave effect with the same quantity of the various keratin-reducing components. Consequently, the wave performance attained with an agent formulated in accordance with the invention can be achieved in this way with significant reduction of the proportion of the keratin-reducing substance and thus with additional protection of the hair and scalp.

Two- and multi-phase systems that can be used in accordance with the invention are systems in which at least two separate continuous phases are present. Examples of such systems are preparations comprising the following phases:

- an aqueous phase and a non-aqueous phase, which are present separately form one another
- an aqueous phase and two non-aqueous phases immiscible with one another, which are each present separately
- an oil-in-water emulsion and a non-aqueous phase present separately from the emulsion
- a water-in-oil emulsion and an aqueous phase present separately from the emulsion.

No two-phase systems in the sense of the present invention are systems in which only one continuous phase is present, such as pure oil-in-water or water-in-oil emulsions.

It has also proven to be advantageous when the agents according to the invention contain a nourishing active substance selected from protein hydrolysates and derivatives thereof. Suitable protein hydrolysates are, in particular, elastin, collagen, keratin, milk, protein, silk protein, soya protein, almond protein, pea protein, potato protein, oat protein, maize protein and wheat protein hydrolysates. Plant-based products can be preferred in accordance with the invention.

Suitable derivatives are, in particular, quaternised protein hydrolysates. Examples of this class of compounds are the products available on the market under the names Lamequat L (CTFA name: Lauryldimonium Hydroxypropylamino Hydrolyzed Animal Protein; Grunau), Croquat®WKP and Gluadin®WQ. The last-mentioned plant-based product can be preferred.

The protein derivatives are contained in the agents according to the invention preferably in quantities of from 0.1 to 10% by weight, based on the total quantity of the agent. Quantities of from 0.1 to 5% by weight are preferred.

The agents according to the invention preferably also contain at least one conditioning active substance.

Cationic polymers are preferred conditioning active substances. These are generally polymers which contain a quaternary nitrogen atom, for example in the form of an ammonium group.

Preferred cationic polymers are, for example,

Quaternised cellulose derivatives, as are commercially obtainable under the names Celquat® and polymer JR®. The compounds Celquat® H 100, Celquat® L 200 and polymer JR® 400 are preferred quaternised cellulose derivatives.

Polysiloxanes with quaternary groups.

Polymers of dimethyl diallyl ammonium salts and copolymers thereof with esters and amides of acrylic acid and methacrylic acid. The commercially obtainable products under the names Merquat®100 (poly(dimethyl diallyl ammonium chloride)) and Merquat®550 (dimethyl diallyl ammonium chloride actylamide copolymer) are examples of cationic polymers this type.

Copolymers of vinyl pyrrolidone with quaternised derivatives of dialkylamino acrylate and methacrylate, such as vinyl pyrrolidone dimethyl amino methacrylate copolymers quaternised with diethyl sulphate. Such compounds are commercially obtainable under the names Gafquat®734 and Gafquat®755.

Vinyl pyrrolidone-vinyl imidazolinium methochloride copolymers, as are sold under the name Luviquat®.

Quaternised polyvinyl alcohol and the polymers known under the names

Polyquaternium 2,
Polyquaternium 17,
Polyquaternium 18 and
Polyquaternium 27 with quaternary nitrogen atoms in the main polymer chain.

Amphopolymers are also suitable as conditioning active substances. The encompassing term amphopolymers includes amphoteric polymers, i.e. polymers which contain both free amino groups and free —COOH or $SO_3H$ groups in the molecule and are capable of forming inner salts, zwitterionic polymers which contain quaternary ammonium groups and —COO$^-$ or —$SO_3^-$ groups, and polymers which contain —COOH or $SO_3H$ groups and quaternary ammonium groups. One example of an amphopolymer that can be used in accordance with the invention is the acrylic resin obtainable under the name Amphomer®, which constitutes a copolymer of tert.-butylaminoethyl methacrylate, N-(1,1,3,3-tetramethylbutyl)acrylamide and two or more monomers from the group composed of acrylic acid, methacrylic acid and simple esters thereof. Amphopolymers that are likewise preferred are composed of unsaturated carboxylic acids (for example acrylic and methacrylic acid), cationically derived unsaturated carboxylic acids (for example acrylamidopropyl trimethylammonium chloride) and optionally further ionic or non-ionogenic monomers. Terpolymers of acrylic acid, methacrylate and methacrylamidopropyltrimonium chloride, as are commercially obtainable under the name Merquat®2001 N and the commercial product Merquat®280 are amphopolymers that are particularly preferred in accordance with the invention.

The cationic or amphoteric polymers are contained in the preparations according to the invention preferably in quantities of from 0.1 to 5% by weight, based on the total preparation.

Silicone gums, such as the trade product Fancorsil® LIM-1, and anionic silicones, such as the product Dow Corning®1784, are also suitable as conditioning active substances.

Examples of the cationic surfactants that can be used as conditioning active substances in the agents according to the invention are, in particular, quaternary ammonium compounds. Ammonium halides are preferred, in particular chlorides and bromides, such as alkyl trimethyl ammonium chlorides, dialkyl dimethyl ammonium chlorides, and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride. The quaternary ester compounds, which can be biologically degraded very effectively, i.e. what are known as "esterquats", such as the methyl hydroxyalkyl dialkoyloxyalkyl ammonium methosulphates sold under the trade names Dehyquart® and Stepantex®, can also be used.

Alkylamidoamines, in particular fatty acid amidoamines, such as the stearyl amidopropyl dimethylamine obtainable under the name Tego Amid®S 18, are characterised, besides a good conditioning effect, especially by their good biological degradability.

It may also be preferable to colour the individual phases with dyes in order to attain particularly good aesthetics. These dyes are preferably only soluble in the aqueous or only in at least a non-aqueous phase in a quantity that leaves a corresponding coloration visible to the observer. It is also possible to colour both the non-aqueous and the aqueous phase with different dyes, preferably in different colours. The colouring of just a non-aqueous phase, however, is preferred.

Further conventional constituents for the agents according to the invention are:

Anionic surfactants, such as soaps, alkyl sulphates and alkyl polyglycol ether sulphates, salts of ethercarboxylic acids of formula R—O—$(CH_2—CH_2O)_x$—$CH_2$—COOH, in which R is a linear alkyl group having 10 to 22 C atoms and x=0 or 1 to 16, acyl sarcosides, acyl taurides, acyl isethionates, sulfosuccinic acid mono and dialkyl esters, linear alkanesulfonates, linear alpha-olefin sulfonates, alpha-sulfo fatty acid methyl esters, and esters of tartaric acid and citric acid, alkyl glycosides or alcohols which constitute addition products of approximately 2-15 molecules of ethylene oxide and/or propylene oxide with fatty alcohols having 8 to 22 C atoms.

Zwitterionic surfactants, such as betaines and 2-alkyl-3-carboxymethyl-3-hydroxyethyl imidazolines.

Ampholytic surfactants, such as N-alkyl glycines, N-alkyl propionic acids, N-alkyl amino butyric acids, N-alkyl imino dipropionic acids, N-hydroxyethyl-N-alkyl amido propyl glycines, N-alkyl taurines, N-alkyl sarcosines, 2-alkyl amino propionic acids, and alkyl amino acetic acids.

Non-ionic surfactants, such as addition products of from 2 to 30 mol ethylene oxide and/or 0 to 5 mol propylene oxide with linear fatty alcohols having 15 to 22 C atoms, with fatty acids having 12 to 22 C atoms, and with alkylphenols having 8 to 15 C atoms in the alkyl group, $C_{12}$-$C_{22}$ fatty acid mono and diesters of addition products of from 1 to 30 mol ethylene oxide with glycerol, $C_8$-$C_{22}$ alkylmono and oligoglycosides and ethoxylated analogues thereof, and addition products of from 5 to 60 mol ethylene oxide with castor oil and hardened castor oil.

Non-ionic polymers, such as vinyl pyrrolidone/vinyl acrylate copolymers, polyvinyl pyrrolidone and vinyl pyrrolidone/vinyl acetate copolymers.

Anionic polymers, such as polyacrylic and polymethacrylic acids, salts thereof, copolymers thereof with acrylic acid and methacrylic acid esters and amides, and derivatives thereof obtained by cross-linking with polyfunctional agents, polyoxy carboxylic acids, such as polyketo and polyaldehyde carboxylic acids and salts thereof, and polymers and copolymers of crotonic acid with esters and amides of acrylic and methacrylic acid, such as vinyl acetate-cotonic acid and vinyl acetate-vinyl propionate-crotonic acid copolymers, Organic thickening agents, such as agar-agar, guar gum, alginates, cellulose ethers such as methyl and methyl hydroxyl propyl cellulose, gelatins, pectins, and/or xanthan gum. Ethoxylated fatty alcohols, in particular those with limited homologue distribution, as are available on the market for example as commercial product under the name Arlypon®F (Henkel), alkoxylated methylglucoside esters, such as the commercial product Glucamate® DOE 120 (Amerchol), and ethoxylated propylene glycol ester, such as the commercial product Antil® 141 (Goldschmidt), can be preferred organic thickening agents.

Structuring substances such as glucose and maleic acid.

Hair-conditioning compounds such as phospholipids, for example soy lecithin, egg lecithin and cephalin.

Perfume oils.

Solubilisers, such as ethanol, isopropanol, ethylene glycol, propylene glycol, glycerol, diethylene glycol and ethoxylated triglycerides and fatty alcohol ethoxylates and derivatives thereof.

Anti-dandruff active substances, such as climbazole, piroctone, olamine and zinc omadine.

Active substances such as bisabolol, allantoin, panthenol, niacinmide, tocopherol and plant extracts.

Light stabilisers.

Consistency promoters, such as sugar esters, polyol esters or polyol alkyl ethers.

Fatty acid alkanolamides.

Complexing agents, such as EDTA, NTA, β-alanine diacetic acid, and phosphonic acids, Swelling and penetration agents, such as PCA, glycerol, propylene glycol monoethyl ether, carbonates, hydrogen carbonates, guanidine, urea and primary, secondary and tertiary phosphates.

Turbidity agents, such as latex or styrene/acrylamide copolymers.

Pearlescent agents, such as ethylene glycol mono and distearate or PEG-3 distearate.

substantive dyes, and

Propellants, such as propane-butane mixtures, $N_2O$, dimethyl ether, $CO_2$, and air.

Furthermore, the agents (a), (b) and/or (c) according to the invention can contain further active substances, auxiliaries and additives, such as non-ionic polymers, for example vinyl pyrrolidone/vinylacrylate copolymers, polyvinyl pyrrolidone, vinylpyrrolidone/vinylacetate copolymers, polyethylene glycols and polysiloxanes; additional silicones such as volatile or non-volatile, straight-chain, branched or cyclic, cross-linked or un-cross-linked poly alkyl siloxanes (such as dimethicones or cyclomethicones), poly aryl siloxanes and/or polyalkyl aryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane (A)-polyoxyalkylene (B) block copolymers, grafted silicone polymers; cationic polymers such as quaternised cellulose ethers, polysiloxanes with quaternary groups, dimethyl diallyl ammonium chloride polymers, acrylamide-dimethyl diallyl ammonium chloride copolymers, dimethylaminoethyl methacrylate-vinyl pyrrolidone copolymers quaternised with diethyl sulphate, vinyl pyrrolidone-imidazolinium-methochloride copolymers, and quaternised polyvinyl alcohol; zwitterionic and amphoteric polymers; anionic polymers such as polyacrylic acids or cross-linked polyacrylic acids; structuring substances such as glucose, maleic acid and lactic acid, hair-conditioning compounds such as phospholipids, for example lecithin and cephalin, dimethyl isosorbide and cyclodextrins; fibre structure-improving active substances, in particular mono, di, and oligosaccharides, for exampleglucose, galactose, fructose, fruit sugars and lactose; dyes for colouring the agent; anti-dandruff active substances such as piroctone olamine, zinc omadine and climbazole; amino acids and oligopeptides; animal-based and/or plant-based protein hydrolysates and protein hydrolysates in the form of their fatty acid condensation products or optionally anionically or cationically modified derivatives; vegetable oils; light stabilisers and UV blockers; active substances such as panthenol, pantothenic acid, pantolactone. allantoin, pyrrolidone carboxylic acids and salts thereof, and bisabolol; polyphenols, in particular hydroxycinnamic acids, 6,7-dihydroxycoumarin, hydroxybenzoic acids, catechins, tannins, leukoanthocyanidins, anthocyanidins, flavanones, flavones and flavonols; ceramides or pseudoceramides; vitamins, pro-vitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; turbidity agents such as latex, styrene/PVP and styrene/acrylamide copolymers; pearlescent agents such as ethylene glycol mono- and distearate and PEG-3 distearate; pigments as well as propellants such as propane-butane mixtures, N2O, dimethyl ether, CO2 and air.

A person skilled in the art will select these further substances in accordance with the desired properties of the agents. With regard to further optional components and the used quantities of these components, reference is made expressly to the relevant handbooks known to a person skilled in the art. The additional active substances and auxiliaries are used in the agents according to the invention preferably in quantities of, in each case, from 0.0001 to 25% by weight, in particular from 0.0005 to 15% by weight, based on the total weight of the application mixture.

As already described previously, the focus of the present invention lies in finding methods (and in the provision of appropriate kits-of-parts) for permanently changing the shape of keratin fibres, which methods and kits-of-parts have a particularly strong deforming effect, but which at the same time damage the keratin fibres to a minimal extent.

During the course of the work carried out for this invention, it was found that the use of metal salts in one or more agents (a), (b) and/or (c) can have a very positive influence on the wave effect, but is linked to the disadvantage of a disproportionately high level of damage to the hair. Keratin fibres which were permanently deformed with use of a metal salt in one of the agents (a) and/or (b) were indeed curled to start with, however the keratin fibres became extremely brittle and fragile, in particular following application of the hydrogen peroxide-containing fixing agent (c).

For this reason, it is particularly preferred when both the permanent waving agent (a) and the intermediate treatment agent (b) and the fixing agent (c) are substantially free from divalent and trivalent metal salts.

In a further preferred embodiment, a method and kit-of-parts according to the invention are therefore characterised in that the permanent waving agent (a) is substantially free from divalent and trivalent metal salts, and the cosmetic agent (b) is substantially free from divalent and trivalent metal salts, and the fixing agent (c) is substantially free from divalent and trivalent metal salts.

Divalent and trivalent metal salts in the sense of the present invention are understood to mean all divalent and trivalent salts of metals from subgroups 3 to 12, and main groups 3 and 4, which are, in particular salts of metals of the $4^{th}$ subgroup: Ti, Zr, Hf
salts of metals of the $5^{th}$ subgroup: V, Nb, Ta
salts of metals of the $6^{th}$ subgroup: Cr, Mo, W
salts of metals of the $7^{th}$ subgroup: Mn
salts of metals of the $8^{h}$ subgroup: Fe, Ru, Os
salts of metals of the $9^{th}$ subgroup: Co, Rh, Ir
salts of metals of the $10^{th}$ subgroup: Ni, Pd, Pt
salts of metals of the $11^{th}$ subgroup: Cu, Ag, Au
salts of metals of the $12^{th}$ subgroup: Zn
salts of metals of the $3^{rd}$ main group: Al, Ga, In, Tl salts of metals of the $4^{th}$ main group: Ge, Sn, Pb (silicon compounds are not considered to be metal salts in the sense of the invention)
salts of metals of the $5^{th}$ main group: As, Sb, Bi Divalent metal salts are understood to be the salts of a twice positively charged metal cation. Trivalent metal salts are understood to be the salts of a thrice positively charged metal cation. In particular, the presence of ($TiO_2$, $MnCl_2$, $MnCl_3$, $Mn(OH)_2$, $Mn(OH)_3$, $FeCl_2$, $FeCl_3$, $Fe(OH)_2$, $Fe(OH)_3$, $CuCl_2$, $Cu(OH)_2$, $ZnCl_2$, $Zn(OH)_2$, $AlCl_3$, $Al(OH)_3$ has proven to be disadvantageous in this context.

The term "substantially free from" is understood to mean that, although certain raw substances in some circumstances could contain metal salts as by-products in small quantities, the deliberate addition of the metal salts to the agents (a), (b) and (c) is avoided.

A preferred embodiment is therefore constituted by a method and kit-of-parts according to the invention which are characterised in that the permanent waving agent (a)—based on the total weight of the agent (a)—includes divalent and trivalent metal salts in a total content of less than 0.1% by weight, preferably less than 0.01% by weight, the cosmetic agent (b)—based on the total weight of the agent (b)—includes divalent and trivalent metal salts in a total content of less than 0.1% by weight, preferably less than 0.01% by weight, the fixing agent (c)—based on the total weight of the agent (c)—includes divalent and trivalent metal salts in a total content of less than 0.1% by weight, preferably less than 0.01% by weight.

In the previously described method according to the invention, at least the agents (a), (b) and (c) are used, and the previously described kit-of-parts comprises the containers (A), (B) and (C) packaged separately.

Besides these three agents or containers, the method or kit-of-parts can also comprise further agents—for example a fourth container (D) containing a fourth agent (d). This agent can be a conditioning agent or a shampoo (d) matched especially to the method, which can be applied following the agent (c). It is also conceivable to use the fourth agent (d) as a pre-treatment agent, which is applied to the keratinic fibres before the application of the agent (a).

The agents (a), (b) and (c) are not mixed with one another, but are applied in succession. For this reason, each of the agents is provided to the user advantageously in a quantity which makes it possible to cover all hair parts that are to be treated to a sufficient extent. By way of example, the agents (a), (b) and (c) can each be present in the containers (A), (B) and (C) in a quantity of from 10 ml to 500 ml, preferably from 20 ml to 250 ml, and particularly preferably from 50 ml to 200 ml.

In principle, there is no time limit for the sequence of steps A1) to C3). Under consideration of any damage to the keratin fibres, however, performing steps A1) to A3) and C1) to C3) at too great an interval from one another over time should be avoided. For this reason, steps A1) to C3) are preferably the steps of a permanent deformation method which the user should carry out in full, where possible, within 48 hours, preferably within 24 hours, more preferably within 12 hours, and particularly preferably within 3 hours.

In a further preferred embodiment a method according to the invention is therefore characterised in that all method steps A1) applying a permanent waving agent (a) to the keratinic fibres, A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres
are carried out within 48 hours, preferably within 24 hours, more preferably within 12 hours, and particularly preferably within 3 hours.

In the prior art an improvement of the deformation result by means of thermal assistance is also described, i.e. the wave effect is intensified, where applicable, in that the keratinic fibres are heated to a higher temperature in a range of from 50 to 220° C. A heating of the keratin fibres can be implemented for example by using a hairdryer, a heat hood, or a straightening iron. In this regard it has been found that thermal assistance when carrying out the method according to the invention also leads to overproportionally severe hair damage. For this reason, all of steps A1) to C3) are particularly preferably carried out at a temperature of at most 80° C., more preferably at most at 60° C., even more preferably at most at 50° C., and particularly preferably at most at 45° C.

In a further preferred embodiment a method according to the invention is therefore characterised in that all method steps
A1) applying a permanent waving agent (a) to the keratinic fibres,
A2) leaving the permanent waving agent (a) to take effect for a period of from 2 to 60 minutes,
A3) rinsing out the permanent waving agent (a) from the keratinic fibres,
B1) applying a cosmetic agent (b) to the keratinic fibres,
B2) leaving the cosmetic agent (b) to take effect for a period of from 2 to 60 minutes,
B3) rinsing out the cosmetic agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres
are carried out at a temperature of at most 80° C., preferably at most at 60° C., more preferably at most at 50° C., and particularly preferably at most at 45° C.

A further subject of the present invention is lastly the use of aliphatic $C_2$-$C_8$ dicarboxylic acids and/or the physiologically acceptable salts hereof to intensify the effect of permanent shape-changing agents on human hair.

With regard to further preferred embodiments of the method according to the invention, that which has been said with regard to the method and kit according to the invention applies, mutatis mutandis.

EXAMPLES

The formulations of the examples below were produced by mixing the raw substances (all values in % by weight)

1.) Permanent Waving Agent (a)

| Ingredients | (a1) | (a2) | (a3) |
|---|---|---|---|
| ammonium thioglycolate[1] | 12.0 | 18.0 | 18.0 |
| sodium bicarbonate | 3.0 | 5.0 | — |
| ammonium bicarbonate | — | — | 8.8 |
| ammonia 25%[2] | — | — | 1.8 |
| Turpinal SL[3] | 0.1 | 0.1 | 0.3 |
| water | to 100 | to 100 | to 100 |

The following raw substances were used:
[1]aqueous solution with 71% by weight active substance
[2]aqueous 25% solution
[3]1-hydroxyethane-1,1-diphosphonic acid, aqueous solution with approximately 60% active substance (INCI name: Etidronic Acid) (Solutia)

2.) Intermediate Treatment Agent (b)

| Ingredients | (b1) | (b2) | (b3) |
|---|---|---|---|
| maleic acid | 15.0 | — | — |
| succinic acid | — | 10.0 | 10.0 |
| monoethanolamine | 11.0 | — | — |
| potassium hydroxide | — | 5.0 | 5.0 |
| L-arginine | 0.3 | 4.0 | 2.0 |
| lysine | — | — | 2.0 |
| Luviskol K 30[4] | 33.4 | — | — |
| Euxyl PE 9010[5] | 1.0 | 1.0 | 1.0 |
| xanthan gum | — | 0.5 | 0.5 |
| water | to 100 | to 100 | to 100 |

[4]polyvinylpyrrolidone, 30% aqueous solution
[5]preserving agent (phenoxyethanol, ethylhexylglycerin)

3.) Fixing Agent (c)

| Ingredients | (c1) | (c2) | (c3) |
|---|---|---|---|
| phosphoric acid (85% by weight in | 0.95 | 0.95 | 0.95 |
| hydrogen peroxide | 2.0 | 4.0 | 6.0 |
| methylparaben | 0.04 | 0.04 | 0.04 |
| Dehyquart A-CA[7] | 0.3 | 0.3 | 0.3 |
| Polyquaternium-6 | 0.5 | 0.5 | 0.5 |
| Aromox MCD W[8] | 3.00 | 3.00 | 3.00 |
| water | to 100 | to 100 | to 100 |

[7]trimethyl hexadecylammonium chloride (approximately 24-26% active substance; INCI name: Aqua (Water), Cetrimonium Chloride) (Cognis)
[8]N,N-dimethyl-N-coco alkyl amine-N-oxide (approximately 30% active substance; INCI name: Cocamine Oxide) (Akzo Nobel)

4.) Permanent Waving Method

The agents (a1), (b1) and (c1) were each tested on strands of hair in accordance with the following method. The treated strands of hair were assessed in each case by 5 trained individuals. A strand of hair that had been treated similarly with agents (a1) and (c1) (without application of the agent (b1)) was used as reference strand:

| Steps | (E1) | (V1) | (V2) |
|---|---|---|---|
| 1 | agent (a1) apply, leave to take effect for 30 minutes, rinse off | agent (a1) apply, leave to take effect for 30 minutes, rinse off | agent (b1) apply, leave to take effect for 10 minutes, rinse off |

| Steps | (E1) | (V1) | (V2) |
|---|---|---|---|
| 2 | agent (b1) apply, leave to take effect for 10 minutes, rinse off | agent (c1) apply, leave to take effect for 10 minutes, rinse off | agent (a1) apply, leave to take effect for 30 minutes, rinse off |
| 3 | agent (c1) apply, leave to take effect for 10 minutes, rinse off | agent (b1) apply, leave to take effect for 10 minutes, rinse off | agent (c1) apply, leave to take effect for 10 minutes, rinse off |
| Result | Combability and feel significantly improved, significant increase in the wave intensity | No improvement of combability and feel, no improvement of wave intensity | No improvement of combability and feel, no improvement of wave intensity |

Strands of hair were treated similarly with use of agents (a2), (b2) and (c2) and were assessed. A strand of hair that had been treated similarly with agents (a2) and (c2) (without application of the agent (b2)) was used as reference strand:

| Steps | (E2) | (V3) | (V4) |
|---|---|---|---|
| 1 | agent (a2) apply, leave to take effect for 30 minutes, rinse off | agent (a2) apply, leave to take effect for 30 minutes, rinse off | agent (b2) apply, leave to take effect for 10 minutes, rinse off |
| 2 | agent (b2) apply, leave to take effect for 10 minutes, rinse off | agent (c2) apply, leave to take effect for 10 minutes, rinse off | agent (a2) apply, leave to take effect for 30 minutes, rinse off |
| 3 | agent (c2) apply, leave to take effect for 10 minutes, rinse off | agent (b2) apply, leave to take effect for 10 minutes, rinse off | agent (c2) apply, leave to take effect for 10 minutes, rinse off |
| Result | Combability and feel significantly improved, significant increase in the wave intensity | No improvement of combability and feel, no improvement of wave intensity | No improvement of combability and feel, no improvement of wave intensity |

Strands of hair were treated similarly with use of agents (a3), (b3) and (c3) and were assessed. A strand of hair that had been treated similarly with agents (a3) and (c3) (without application of the agent (b3)) was used as reference strand:

| Steps | (E3) | (V5) | (V6) |
|---|---|---|---|
| 1 | agent (a3) apply, leave to take effect for 30 minutes, rinse off | agent (a3) apply, leave to take effect for 30 minutes, rinse off | agent (b3) apply, leave to take effect for 10 minutes, rinse off |
| 2 | agent (b3) apply, leave to take effect for 10 minutes, rinse off | agent (c3) apply, leave to take effect for 10 minutes, rinse off | agent (a3) apply, leave to take effect for 30 minutes, rinse off |
| 3 | agent (c3) apply, leave to take effect for 10 minutes, rinse off | agent (b3) apply, leave to take effect for 10 minutes, rinse off | agent (c3) apply, leave to take effect for 10 minutes, rinse off |
| Result | Combability and feel significantly improved, significant increase in the wave intensity | No improvement of combability and feel, no improvement of wave intensity | No improvement of combability and feel, no improvement of wave intensity |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for permanently changing the shape of keratinic fibres, comprising the following steps in the specified order A1) applying a permanent waving agent (a) to the keratinic fibres, A2) leaving the permanent waving agent (a) to take effect for a period of from 2 to 60 minutes,
A3) rinsing out the permanent waving agent (a) from the keratinic fibres,
B1) applying a intermediate treatment agent (b) to the keratinic fibres, wherein the intermediate treatment agent (b)—based on the total weight of the intermediate treatment agent (b)—includes
   (b1) 7.5 to 17.5% by weight of maleic acid and/or succinic acid, and
   (b2) 1.0 to 10.0% by weight of arginine and/or histidine, and
B2) leaving the intermediate treatment agent (b) to take effect for a period of from 2 to 60 minutes,
B3) rinsing out the intermediate treatment agent (b) from the keratinic fibres,
C1) applying a fixing agent (c) to the keratinic fibres,
C2) leaving the fixing agent (c) to take effect for a period of from 2 to 60 minutes,
C3) rinsing out the fixing agent (c) from the keratinic fibres,
wherein
  the permanent waving agent (a)
   (a1) includes one or more keratin-reducing compounds and
  and
  the fixing agent (c)
   (c1) includes hydrogen peroxide.

2. The method according to claim 1, wherein the keratinic fibres are deformed with the aid of deformation aids before, after, or during step A1), A2), A3), B1), B2), B3), C1) C2) or C3).

3. The method according to claim 1, wherein all method steps are carried out within 48 hours.

4. The method according to claim 1, wherein the permanent waving agent (a) includes (a1) one or more keratin-reducing compounds from the group of thioglycolic acid, thiolactic acid, thiomalic acid, cysteine, cysteamine, cysteine, 2-mercaptoethanesulfonic acid and the physiologically acceptable salts thereof.

5. The method according to claim 1, wherein the permanent waving agent (a) includes (a1) one or more keratin-reducing compounds selected from the group consisting of thioglycolic acid, ammonium thioglycolate, thiolactic acid and ammonium thiolactate.

6. The method according to claim 1, wherein the permanent waving agent (a)—based on the total weight of the permanent waving agent (a) (a1) includes one or more keratin-reducing compounds in a total quantity of from 1.5 to 20.0% by weight.

7. The method according to claim 1, wherein the fixing agent (c)—based on the total weight of the agent (c)—includes (c1) 1.0 to 15.0% by weight of hydrogen peroxide.

8. The method according to claim 1, wherein the permanent waving agent (a) is substantially free from divalent and trivalent metal salts, the intermediate treatment agent (b) is substantially free from divalent and trivalent metal salts, and the fixing agent (c) is substantially free from divalent and trivalent metal salts.

* * * * *